United States Patent [19]

Churchill et al.

[11] Patent Number: 5,834,178
[45] Date of Patent: Nov. 10, 1998

[54] FLUSH-STORAGE SOLUTION FOR DONOR ORGANS

[75] Inventors: Paul C. Churchill, Troy; Monique C. Churchill, St. Clair Shores, both of Mich.

[73] Assignee: Wayne State University, Detroit, Mich.

[21] Appl. No.: 890,269

[22] Filed: Jul. 9, 1997

[51] Int. Cl.$^6$ ....................................................... A01N 1/02
[52] U.S. Cl. .............................................. 435/1.2; 435/1.1
[58] Field of Search ............................. 435/1.2, 325, 1.1; 514/23

[56] References Cited

U.S. PATENT DOCUMENTS

| | | |
|---|---|---|
| 4,798,824 | 1/1989 | Belzer et al. . |
| 4,873,230 | 10/1989 | Belzer et al. . |
| 4,879,283 | 11/1989 | Belzer et al. . |
| 4,920,044 | 4/1990 | Bretan, Jr. . |
| 4,994,444 | 2/1991 | Zikria . |
| 5,002,965 | 3/1991 | Ramwell et al. . |
| 5,082,831 | 1/1992 | Leaf et al. . |
| 5,145,771 | 9/1992 | Lemasters et al. . |
| 5,200,398 | 4/1993 | Strasberg et al. . |
| 5,217,860 | 6/1993 | Fahy et al. . |
| 5,306,711 | 4/1994 | Andrews . |
| 5,328,821 | 7/1994 | Fisher et al. . |
| 5,348,945 | 9/1994 | Berberian et al. . |
| 5,370,989 | 12/1994 | Stern et al. . |
| 5,403,834 | 4/1995 | Malfroy-Camine et al. . |
| 5,405,742 | 4/1995 | Taylor . |
| 5,407,793 | 4/1995 | Del Nido et al. . |
| 5,432,053 | 7/1995 | Berdyaev et al. . |
| 5,514,536 | 5/1996 | Taylor . |
| 5,552,267 | 9/1996 | Stern et al. . |
| 5,554,497 | 9/1996 | Raymond . |
| 5,565,317 | 10/1996 | Dohi et al. . |

OTHER PUBLICATIONS

Fresenius AG, "Organ Perfusion 'Euro–Collins Solution' 'Multiorgan perfusion System'", pp. 1–13.

*Primary Examiner*—Toni R. Scheiner
*Attorney, Agent, or Firm*—Thomas S. Borecki; Charles R. Mattenson; Paula J. Kelly

[57] ABSTRACT

A flush-storage solution for flushing blood out of a donor organ and cold-storing the donor organ prior to transplantation is provided. The solution of the present invention includes mannitol as an impermeable solute. The present invention also provides an improved method of flushing and cold-storing donor organs as well as an improved method of transplanting donor organs into a recipient.

24 Claims, 1 Drawing Sheet

FLUSH-STORAGE SOLUTION FOR DONOR ORGANS

BACKGROUND OF THE INVENTION

The present invention relates generally to the transplantation of organs harvested from a donor patient into a recipient patient. More specifically, the present invention relates to chemical solutions used to prepare the donor organs for transplantation. Still more specifically, the present invention relates to chemical solutions used to flush blood from a donor organ after harvesting and for storing the donor organ prior to transplantation.

Solutions that are used to treat a donor organ prior to transplantation are known as "flush-storage" solutions, "preservation" solutions and "cold-storage" solutions. These solutions are used to flush the donor's blood out of the donor organ such as a kidney, liver, pancreas, lung, etc. These solutions are also used to cool the organs down for storage prior to transplantation. Further, these solutions are used for storing the donor organs prior to transplantation.

The two most commonly used flush-storage solutions are known as the "Euro-Collins" solution which is manufactured and sold by Fresenius AG of Germany and VIASPAN® solution which was developed by Belzer at the University of Wisconsin and which is manufactured and sold by the Du Pont Merck Pharmaceutical Company. The VIASPAN® solution is also commonly referred to as the "Belzer UW" solution or the "Belzer" solution. The Euro-Collins and the Belzer solutions have two common features. First, both solutions include high levels of potassium and both solutions have a pH at room temperature of about 7.4.

Flush-storage solutions typically include high concentrations of potassium like the Euro-Collins solution and the Belzer solution because the storage of the donor organ at low temperature results in hypothermia in the organ and hypothermia promotes the loss of potassium from isolated-perfused rat kidneys. Loss of potassium can be prevented by increasing the extra cellular concentration of potassium in the flush-storage solution.

However, solutions with high concentrations of potassium can be dangerous if the potassium remains in the organ during the transplantation surgery. Specifically, the extra potassium can be flushed into the recipient's blood stream which can result in cardiac arrest.

The Euro-Collins and Belzer solutions also employ relatively high concentrations of impermeable solutes in order to prevent water uptake or swelling after transplantation. Essentially, combinations of various impermeable carbohydrates and anions are used to prevent the tissue swelling. For example, the Euro-Collins solution utilizes 180–198 mM glucose and 58 mEq phosphate while the Belzer solution utilizes 30 mM raffinose, 100 mM lactobionate, 25 mM phosphate and 5 mM sulfate. An earlier solution, known as the "Collins" solution contained high concentrations of phosphate (100 mEq) and magnesium (60 mEq) which reportedly caused crystalline deposits to form on the renal vasculature during the storage period.

The Belzer solution also teaches the addition of hydroxyethylstarch as a colloid oncotic support against interstitial edema. However, hydroxyethylstarch has been reported to remove vascular endothelial cells from homothermic isolated-profused rabbit kidneys. Fuller et al., J. Surg. Res., 22:128–142 (1977). Thus, the possibility that hydroxyethylstarch might be damaging to the organ to be transplanted justifies omitting it from a flush-storage solution.

While the substitution of impermeable carbohydrates and anions by the Euro-Collins and Belzer solution may have eliminated the crystallization problem, the Euro-Collins and Belzer solutions still provide limited storage capabilities. Specifically, while the Euro-Collins and Belzer solution provide good glomerular filtration rates (GFR) when a kidney is transplanted immediately after harvest, the GFRs of transplanted kidneys are substantially less than 100% of normal if the kidneys are subject to a 24 hour period of cold-storage prior to transplantation. Specifically, the GFRs of donor kidneys flushed with the Euro-Collins solution after a 24 hour period of cold-storage prior to transplantation is close to 0%. The GFRs of donor kidneys when flushed with the Belzer solution after a 24 hour period of cold-storage is approximately 60 to 80% of normal.

The Belzer solution also includes additives including allopurinol, glutathione, adenosine and dihydroxyethyl-starch despite the fact that these additives have not been shown to provide beneficial effects on the function of transplanted kidneys. Specifically, allopurinol inhibits xanthine oxidase, but xanthine oxidase activity is negligible in ischemic renal tissue, Karrow et al., *Organ Preservation for Transplantation*, 2d Ed., pp. 497–515, Marcel Deltker, (1981), and at the conclusion of the renal ischemia, when allopurinol might do some good, the incoming blood flow would flush it into the body of the recipient instead of maintaining the presence of the allopurinol in the transplanted kidney.

Further, there is no evidence that glutathione is required during cold ischemia and, even if it were, there is no evidence that adding glutathione to extra cellular fluid can provide any benefit. Like allopurinol, glutathione would have a tendency to be flushed into the recipient's circulation once the renal blood flow began.

Similarly, adenosine appears to be a non-beneficial additive and may even play a pathogenic role in acute renal failure. Further, adding adenosine to a flush-storage solution has been shown to produce a prolonged decrease in the GFR of transplanted rabbit kidneys. Bhul et al., Life Science, 19:1889–1896 (1976). Also, the entry of adenosine into a recipient's circulation may produce adverse cardiovascular reactions. Van Renterghem et al., Lancet, 2:745 (1989). Hence, the addition of adenosine in flush-storage solutions appears to be unwarranted.

Accordingly, no currently available flush-storage solution provides the benefits of a low potassium formulation with an improved impermeable solute without the unnecessary and potentially harmful additives utilized by the Belzer solution. Accordingly, there is a need for an improved low potassium flush-storage solution with an improved impermeable solute and with a minimum of additives.

SUMMARY OF THE INVENTION

The present invention provides a flush-storage solution for use in flushing blood out of a donor organ, cooling a donor organ and storing a donor organ prior to transplantation. The solution of the present invention comprises an aqueous solution of mannitol in an amount ranging from about 50 mM to about 100 mM.

In an embodiment, the solution of the present invention further comprises sodium in an amount ranging from about 130 mM to about 160 mM.

In an embodiment, the solution of the present invention further comprises potassium in an amount less than 6 mM.

In an embodiment, the solution of the present invention has a pH ranging from about 6.6 to about 7.0 at a temperature of about 0° C.

In an embodiment, the solution of the present invention has a pH ranging from about 6.7 to about 6.9 at a temperature of about 0° C.

In an embodiment, the present invention comprises about 4 mM potassium.

In an embodiment, the sodium content of the present invention ranges from about 138 mM to about 141 mM.

In an embodiment, the mannitol concentration of the solution of the present invention is about 50 mM.

In an embodiment, the present invention further comprises glucose in an amount that is less than 20 mM.

In an embodiment, the present invention comprises about 10 mM glucose.

In an embodiment, the present invention comprises lactobionate in an amount exceeding 100 mM.

In an embodiment, the present invention comprises lactobionate in an amount ranging from about 120 mM to about 160 mM.

In an embodiment, the present invention comprises about 140 mM lactobionate.

In an embodiment, the present invention further comprises glycine.

In an embodiment, the present invention further comprises glycine in an amount ranging from about 2 mM to about 10 mM.

In an embodiment, the present invention comprises about 5 mM glycine.

In an embodiment, the present invention comprises, sodium, potassium, magnesium, lactobionate, sulfate, phosphate, glucose, mannitol, glycine and heparin and does not include additional additives such as raffinose, glutathione, adenosine, hydroxyethylstarch, allopurinol, insulin or dexamethasone.

In an embodiment, the solution of the present invention has a calculated osmolality ranging from about 340 mOs/Kg to about 390 mOs/Kg.

In an embodiment, the phosphate concentration of the present invention is less than 10 mM.

In an embodiment, the phosphate concentration of the present invention ranges from 0 or close to 0 to about 5 mm.

In an embodiment, the solution of the present invention further comprises magnesium in an amount less than 10 mM.

In an embodiment, the present invention comprises about 5 mM magnesium.

In an embodiment, the sulfate concentration of the present invention is less than 10 mM.

In an embodiment, the solution of the present invention further comprises about 5 mM sulfate.

In an embodiment, the solution of the present invention comprises sodium in an amount ranging from about 130 mM to about 150 mM, potassium in an amount less than 6 mM, mannitol in an amount ranging from about 50 mM to about 100 mM, a pH ranging from about 6.7 to about 6.9 and being substantially free of allopurinol, glutathione, adenosine and hydroxyethylstarch.

The present invention also includes a method of preparing a donor organ for transplantation. A method of the present invention comprises the steps of flushing the donor's blood out of the organ with a solution that comprises mannitol in an amount ranging from about 50 mM to about 100 mM, sodium in an amount ranging from about 130 mM to about 160 mM, and potassium in an amount less than 6 mM, followed by the step of storing the organ in said solution.

The present invention also provides a method of transplanting a donor organ into a recipient patient comprising the steps of harvesting the organ from a donor, flushing the donor's blood out of the organ with a solution comprising mannitol in an amount ranging from about 50 mM to about 100 mM, sodium in an amount ranging from about 130 mM to about 160 mM, and potassium in an amount less than 6 mM, followed by the steps of storing the organ in said solution and transplanting the organ into the recipient.

It is therefore an advantage of the present invention to provide a flush-storage solution that utilizes mannitol as an impermeable solute.

It is therefore an advantage of the present invention to provide a low potassium flush-storage solution.

Another advantage of the present invention is to provide a flush-storage solution which utilizes sodium as a substitute for potassium.

Another advantage of the present invention is to provide a flush-storage solution without additives including glutathione, adenosine, hydroxyethylstarch, allopurinol, insulin and dexamethasone.

Another object of the present invention is to provide an improved flush-storage solution with a mildly acidic pH.

Yet another advantage of the present invention is to provide a flush-storage solution that improves the glomerular filtration rates of transplanted kidneys and preserves the function of other organs that have been flushed and stored with the flush-storage solution of the present invention.

Another advantage of the present invention is an improved method of flushing and storing donor organs.

Another advantage of the present invention is an improved method of transplanting donor organs.

Additional features and advantages of the present invention are described in, and will be apparent from, the detailed description of the presently preferred embodiments and upon reference to the accompanying figures and tables.

DETAILED DESCRIPTION OF THE PRESENTLY PREFERRED EMBODIMENTS

Figure 1:
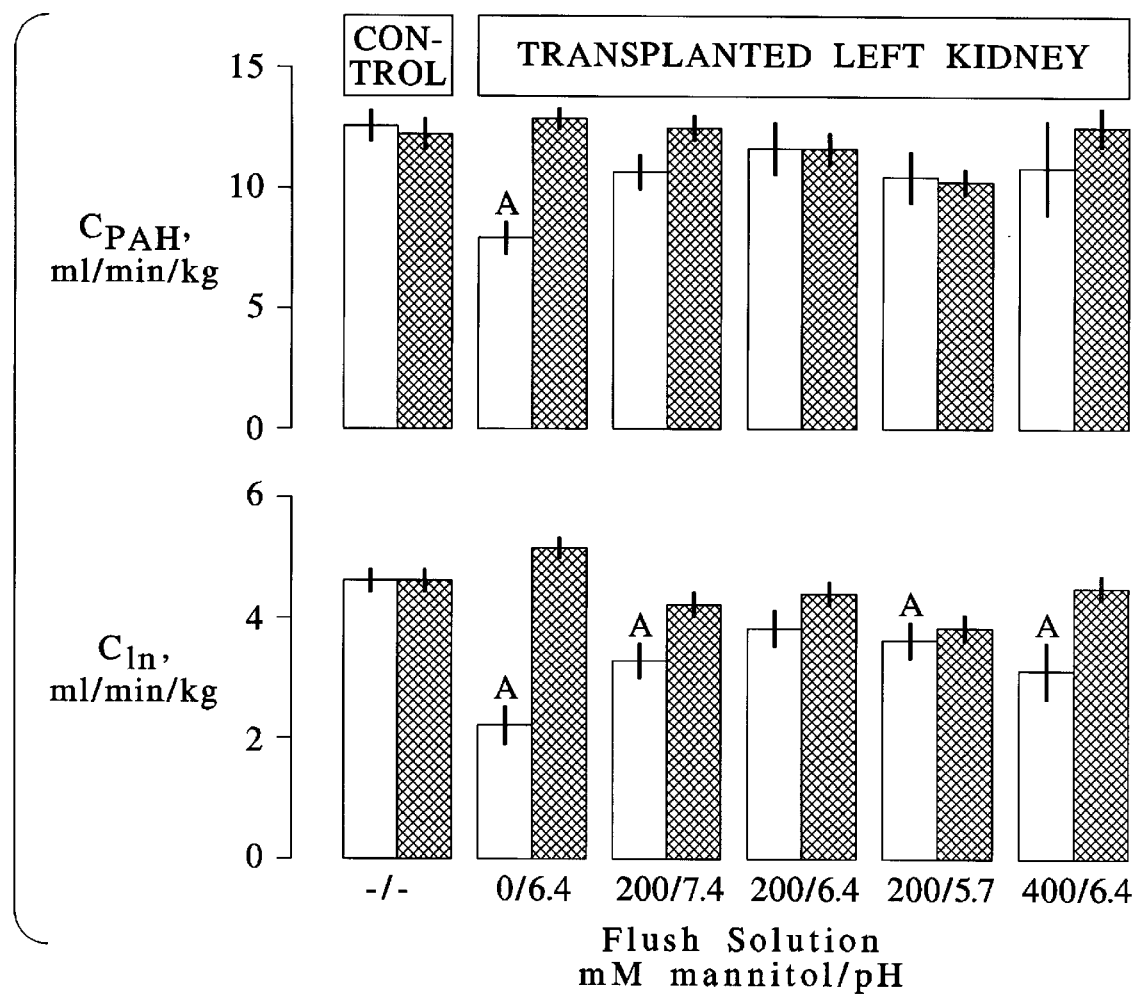
FIGS. 1 and 2 show para-aminohippuric acid clearances ($C_{PAH}$) and inulin clearances ($C_{IN}$) in control rats (native left kidney open bar, versus native right kidney crosshatched bar) and in five groups of experimental rats (transplanted left kidney open bar, versus native right kidney crosshatched bar). Before transplantation, kidneys were flushed with one of five different solutions labeled "0/6.4", "200/7.4", "200/5.7", and "400/6.4" whereas the kidneys of control rats were not flushed (labeled "–/–"). The clearance studies were performed one week post-transplant. The results are means ± standard errors, and n=18, 7, 8, 7, 6, and 7 in groups from left to right. "A" indicates p<0.05 compared with the corresponding value in the control group. It can be seen that the flush solution labeled "200/6.4" is superior to the others in that there are no differences between the $C_{PAH}$ and $C_{IN}$ of the transplanted kidneys versus the non transplanted kidneys in control rats. In other words, the transplanted kidneys have normal plasma flows and glomerular filtration rates.

The present invention provides an improved flush-storage solution for removing a donor's blood from a donor organ and for storing the donor organ prior to transplantation. The solution of the present invention comprises mannitol in an amount ranging from about 50 mM to about 100 mM. The inventors of the present invention have found that mannitol provides an effective impermeable solute and provides an excellent substitute for the high concentrations of glucose and phosphate found in the Euro-Collins solution and the raffinose, phosphate and sulfate found in the Belzer solution. In a preferred embodiment, mannitol is present in an amount ranging from about 40 mM to about 60 mM. It will be noted that mannitol in these concentrations serves primarily as an impermeate solute as opposed to a mere anti-oxidant.

One embodiment of the present invention comprises sodium in an amount ranging from about 130 mM to about 160 mM. The inventors of the present invention have found that sodium provides an excellent substitute for the potassium used in high concentrations by prior art flush-storage solutions without the risks associated with using high concentrations of potassium. Further, the use of sodium in accordance with the present invention eliminates the need to thoroughly flush the organ with a different solution or solutions prior to transplantation. In a preferred embodiment, sodium is present in an amount ranging from 138–141 mM.

Preferably, the solution of the present invention includes potassium in an amount similar to the concentration of potassium found in blood, or in an amount ranging from about 3 to about 6 mM. In a preferred solution, potassium is present in a concentration of about 4 mM.

The inventors have found that the solution is preferably slightly acidic having a pH ranging from about 6.6 to about 7.0, and preferably from about 6.7 to about 6.9 at an ice-cold temperature or at a temperature of about 0° C.

The composition of a preferred embodiment of the present invention is shown in the table below along with the compositions of the Euro-Collins and Belzer solutions.

TABLE 1

| | | An Embodiment of Present Invention | Euro-Collins | Belzer |
|---|---|---|---|---|
| $Na^{+1}$ | mM | 138–141 | 10 | 5–20 |
| $K^{+1}$ | mM | 4.5 | 115 | 135–140 |
| $Mg^{+2}$ | mM | 5 | 0 | 5 |
| Lactobionate | mM | 140 | 0 | 100 |
| $HCO_3^{-1}$ | mM | 0 | 10 | 0 |
| $Cl^{-1}$ | mM | 0 | 15–16 | 0–1 |
| $SO_4^{-2}$ | mM | 5 | 0 | 5 |
| $HPO_4^{-2}/H_2PO_4^{-1}$ | mM | 2 | 58 | 25 |
| glucose | mM | 10 | 180–198 | 0 |
| mannitol | mM | 50 | 0 | 0 |
| raffinose | mM | 0 | 0 | 30 |
| glycine | mM | 5 | 0 | 0 |
| glutathione | mM | 0 | 0 | 3 |
| adenosine | mM | 0 | 0 | 5 |
| hydroxyethylstarch | gr/liter | 0 | 0 | 50 |
| allopurinol | mM | 0 | 0 | 1 |
| insulin | units/liter | 0 | 0 | 40 |
| dexamethasone | mg/liter | 0 | 0 | 16 |
| HEPARIN® | units/liter | 3,000 | 0 | 0 |
| pH | | 6.7–6.9 (ice cold) | 7.4 (room temp) | 7.4 (room temp) |
| calculated osmolality | mOs/Kg | 360–371 | 340–360 | 320 |

The inventors have found that the phosphate concentration is not necessary and may be eliminated. The HEPARIN® additive is a combination of heparin (3,000 units/liter), penicillin (220,000 units/liter), and cefazolin (185 mg/liter) which is preferably added to the solution prior to use.

The magnesium concentration of the present invention can range from 0 to 5 and is preferably about 5 mM.

The lactobionate concentration can vary from 100 to 150, is preferably above 100 mM and more preferably within the 135 to 140 range.

The sulfate concentration can vary from 0 to 5.0 and is preferably about 5 mM.

The phosphate concentration can vary from 0 to 10 and preferably falls within the 0 to 5 range.

The glucose concentration can vary from 0 to 10 and is preferably about 10 mM.

The glycine concentration can vary from 0 to 5 and is preferably about 5 mM.

The HEPARIN® concentration can vary from 0 to 10,000 and is preferably about 3000 units/liter.

The solution of the present invention can be prepared in the following way. For example, to make one liter of solution (use refrigerated sterile water for all solutions): dissolve 50.161 grams of lactobionic acid in 350 milliliters of water, and add 133 milliliters of 1 molar NaOH and 16 milliliters of 0.25 Molar KOH with continuous stirring; dissolve 9.11 grams of mannitol in 200 milliliters of water and add this solution to the lactobionate solution with continuous stirring; dissolve together 0.4856 grams of the sodium salt of glycine, 1.2328 grams of $MgSO_4 \cdot 7H_2O$, and 1.8016 grams of glucose in 120 milliliters of water and add this solution to the lactobionate solution with continuous stirring. Add water to the lactobionate solution to yield one liter, and to this, add 0.24 grams of $NaH_2PO_4$. Measure the pH at approximately 0° C. (ice cold) and adjust the pH to 6.7–6.9 with either NaOH (to increase pH) or $NaH_2PO_4$ (to decrease pH). (Note: the pH will drift for 2–3 days after the solution is made). Sterilize the solution by pressure filtration (0.2 μm Sterile Acrodisc: Gelman Sciences). Before use, add heparin (3,000 units per liter), penicillin (220,000 units per liter), and cefazolin (185 mg per liter).

EXPERIMENTAL RESULTS

The inventors have found that the solution of the present invention provides superior results in a rat kidney transplant model in direct comparison with the Euro-Collins (EC) and Belzer University of Wisconsin (UW) solutions, especially when kidneys are subjected to a 24 hour cold storage period before transplantation. Such cold storage periods are common in clinical transplantation.

Figure 2:
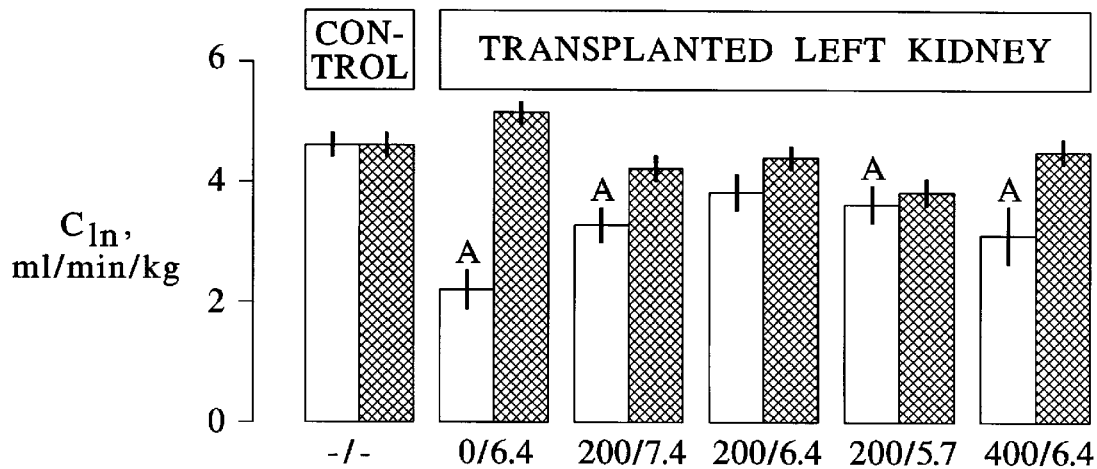

In the first series of experiments, freshly harvested kidneys (that is, the kidneys were not subjected to cold storage) were transplanted into unilaterally nephrectomized recipients, and one week post-transplant, renal function was measured separately in the two kidneys of each rate. This experimental design allowed function of the transplanted kidney to be compared with that of the contralateral intact native kidney, or to the function of kidneys in an intact control rate. Five different flush solutions were used: 150 mM NaCl at pH 6.4 (Group 0/6.4; n=7); 150 mM NaCl plus 200 mM mannitol at pH 6.4 (Group 200/6.4; n=7); 150 mM NaCl plus 400 mM mannitol at pH 6.4 (Group 400/6.4; n=7); 150 mM NaCl plus 200 mM mannitol plus 5 mM sodium phosphate buffer at either pH 5.7 (Group 200/5.7; n=6) or pH 7.4 (Group 200/7.4; n=8). In addition, there was a control group (Group –/–), consisting of eighteen (n=18) rats with both native kidneys intact. FIGS. 1 and 2 show the para-aminohippuric acid clearances ($C_{PAH}$) and inulin clearances ($C_{IN}$) in the control rats (Group –/–); native left kidney open bar, versus native right kidney crosshatched bar) and in the five groups of experimental rats (the Groups labeled as discussed above; transplanted left kidney open bar, versus native right kidney crosshatched bar).

Both kidneys of Group –/– (intact native left and right kidneys) were virtually identical with respect to these parameters, and the left-kidney-to-right-kidney ratios for PAH clearance (1.03±0.02) and for inulin clearance (0.99±0.02) were not significantly different from unity. There were no significant differences among the six groups with respect to PAH clearance or inulin clearance of the native right kidney. However, there were significant differences in left (transplanted) kidney clearances, wither in comparison with the control rats (Group −/−) or in comparison with the contralateral kidneys of the same rats. These comparisons support the three conclusions discussed below.

First, comparisons between Groups 200/7.4, 200/6.4, and 200/5.7 (same NaCl and mannitol concentrations) indicate that pH<7.4 has a beneficial effect, since the left-kidney-to-right-kidney ratios of PAH clearance and inulin clearance in Group 200/5.7 (1.03±0.09 and 0.97±0.09, respectively) were higher than in Group 200/7.4 (0.87±0.07 and 0.80±0.09). In fact, as assessed by these ratios, the PAH and inulin clearances of transplanted kidneys flushed with 150 mM NaCl plus 200 mM mannitol at pH 5.7 were indistinguishable from the PAH and inulin clearances of the contralateral native kidneys. Second, comparison of Group 0/7.4 with all the other transplant groups indicates that a flush solution of 150 mM NaCl alone is inferior to a mannitol-containing flush solution, since the values of left kidney PAH clearance, left kidney inulin clearance, and left-to-right ratios of PAH and inulin clearances were all lower in Group 0/6.4 than in any other transplant group, including Group 200/6.4 (both of these flush solutions had the same pH). Third, similar comparisons between Group 200/6.4 and Group 400/6.4 indicate that a flush solution containing 200 mM mannitol is superior to one containing 400 mM mannitol.

Nearly four dozen (46) different modifications of the best of the above solutions (150 mM NaCl+200 mM mannitol at pH 6.4) and Euro-Collins (EC) and Belzer's University of Wisconsin (UW) solutions were tested in the rate kidney transplant mode. Some were tested using either unilaterally or bilaterally nephrectomized recipients. Kidneys were either flushed with the solution and transplanted immediately (0 hours of cold storage) or they were flushed with the solution and stored ice-cold in the same solution for 24–48 hours before transplantation. Ten days post-transplant, PAH and inulin clearances were measured.

Table 2 shows some of the results in unilaterally nephrectomized recipients (transplanted left kidney, native right kidney; date for the left transplanted kidney is shown) and in a Control group (non-transplanted native left and right kidneys; data for the left native kidney is shown). It can be seen that if kidneys are flushed and transplanted immediately (0 hours storage), EC (Euro-Collins), UW (Belzer's University of Wisconsin), and NaM 1 (unmodified 150 mM NaCl+200 mM mannitol at pH 6.4, or solution "200/6.4" in the experiments discussed above) gave equally good results, in that the inulin clearances ($C_{IN}$) and PAH clearances ($C_{PAH}$) of the transplanted left kidneys were about 80–85% of the control values ($C_{IN}$ and $C_{PAH}$ of the left kidney of control rats). Several modified solutions (NaM 19, 23, and 39) gave even better results in that $C_{IN}$ and $C_{PAH}$ of the transplanted kidneys were more than 100% of control values. Differences between the flush solutions were much more evident if kidneys were subjected to cold storage before transplantation. After 24 hours of cold storage, kidneys flushed with EC or with NaM 1 were non-viable, because ten days post-transplant, $C_{IN}$ and $C_{PAH}$ were zero or virtually zero (thus, although NaM 1, or the unmodified 150 mM NaCl+200 mM mannitol at 6.4, worked well if kidneys were transplanted immediately, it did not work well if kidneys were stored for 24 hours before transplantation). In contrast, $C_{IN}$ and $C_{PAH}$ of transplanted kidneys that had been flushed with and stored for 24 hours in UW (3.01±0.18 and 11.8±0.5, respectively) were about 60–70% of the control values (5.06±0.27 and 16.0±0.80, respectively). However, one of our modified solutions (NaM 39) was clearly superior to either EC or UW, in that $C_{IN}$ and $C_{PAH}$ of the transplanted kidneys were about 78–83% of control values.

Table 3 shows the results in bilaterally nephrectomized recipients (only the solitary transplanted kidney) and in a Control group that had been unilaterally nephrectomized ten days before renal function was measured (only the solitary native kidney). EC was not tested in this preparation because it had failed in the unilaterally nephrectomized recipients if kidneys were subjected to cold storage. Otherwise, the same conclusions can be drawn from the bilaterally nephrectomized recipients as from the unilaterally nephrectomized recipients. Namely, UW and solutions of the present invention give equally good results if kidneys are flushed and transplanted immediately (0 hours of cold storage), in that the $C_{IN}$ and $C_{PAH}$ of transplanted kidneys are virtually 100% of control values. However, after a 24 hour period of cold storage, solutions of the present invention yield higher $C_{IN}$ and $C_{PAH}$ than the UW solution. In fact, kidneys flushed with and stored in solutions of the present invention (NaM 17, 38, 49, and 40) have $C_{IN}$ and $C_{PAH}$ equal to or greater than 100% of the control values.

Altogether, EC, UW, and solutions of the present invention (NaM 1–46) were tested in a total of 288 rat kidney transplant, either unilaterally or bilaterally nephrectomized recipients, and with periods of cold storage ranging from 0 to 48 hours. The data shows that, when kidneys are flushed and transplanted immediately, the composition of the flush solution has little or no effect; all solutions tested gave very good results. However, if kidneys are flushed and cold stored for 24 hours pre-transplant, a cold storage period common in clinical kidney transplantation, EC does not preserve kidney function at all, UW is much better than EC, and solutions of the present invention (NaM 17, 38, 39, 40, 43–46) are even better than UW in that the glomerular filtration rates and plasma flows are higher. With longer periods of cold storage, post-transplant function deteriorates rapidly, independently of the solution. Kidneys cold stored for 48 hours before transplantation are nearly non-functional ten days later, independently of the flush storage solution (UW or any of the solutions of the present invention).

The solution set forth in Table 1 (NaM 39) contains a low concentration of potassium that is not dissimilar to the concentration of potassium found in normal blood. Thus, the solution of the present invention is safer to use than either EC or UW in that there is no possibility of flushing excess potassium into a recipient's blood stream, which could cause cardiac arrest in the recipient. Further, the solution of the present invention does not include the several additives which are present in Belzer UW solution, such as allopurinol, glutathione, and adenosine. Thus, the solution of the present invention is additionally safer to use than UW because glutathione is unstable in UW and adenosine has been found to produce adverse cardiovascular reactions in the recipient if it is flushed into the recipient's circulation as described above.

In conclusion, the solution of the present invention is not only safer to use than either EC or UW, it also better preserves the function of kidneys that are subjected to cold storage before transplantation.

TABLE 2

| Group | Flush solution | n | $C_{In}$ | $C_{PAH}$ |
| --- | --- | --- | --- | --- |
| Control | — | 8 | 5.06 ± 0.27 | 16.0 ± 0.8 |
| 0 hours | EC | 3 | 4.30 ± 0.26 | 13.3 ± 0.9 |
|  | UW | 3 | 4.40 ± 0.75 | 14.0 ± 1.7 |
|  | NaM 1 | 4 | 4.39 ± 0.35 | 14.1 ± 1.1 |
|  | NaM 19, 23, 39 | 4 | 5.94 ± 0.49 | 17.4 ± 0.4 |
| 24 hours | EC | 2 | 0.08 ± 0.08 | 0.3 ± 0.3 |
|  | UW | 6 | 3.01 ± 0.18 | 11.8 ± 0.5 |
|  | NaM 1 | 8 | 0.0 | 0.0 |
|  | NaM 39 | 13 | 4.12 ± 0.34 | 12.4 ± 0.8 |
| 30 hours | NaM 39, 43, 46 | 6 | 1.09 ± 0.57 | 4.0 ± 2.0 |
| 36 hours | NaM 39, 43, 46 | 8 | 0.20 ± 0.12 | 0.7 ± 0.5 |
| 40 hours | NaM 44, 45 | 2 | 0.08 ± 0.07 | 0.3 ± 0.3 |
| 48 hours | UW | 1 | 0.01 | 0.10 |
|  | NaM 40 | 8 | 0.00 | 0.00 |

Clearances of inulin ($C_{In}$) and of PAH ($C_{PAH}$) in native left kidneys of control rats (intact left and right kidneys) and in transplanted left kidneys (unilaterally nephrectomized recipients, intact native right kidney; ten days post-transplant). Kidneys were flushed and transplanted immediately (0 hours) or flushed with and stored in the same solution for 24–48 hours as indicated. See text for description of the solutions.

TABLE 3

| Group | Flush solution | n | $C_{In}$ | $C_{PAH}$ |
| --- | --- | --- | --- | --- |
| Control | — | 12 | 7.45 ± 0.23 | 22.8 ± 1.0 |
| 0 hours | UW | 3 | 7.30 ± 0.61 | 23.1 ± 1.1 |
|  | NaM 17 | 5 | 7.50 ± 0.50 | 25.8 ± 1.6 |
| 24 hours | UW | 10 | 6.08 ± 0.24 | 23.4 ± 0.6 |
|  | NaM 17 | 7 | 7.45 ± 0.21 | 28.5 ± 1.1 |
|  | NaM 38, 39, 40 | 4 | 8.07 ± 0.48 | 29.7 ± 1.9 |

Clearances of inulin ($C_{In}$) and of PAH ($C_{PAH}$) in solitary native left kidneys of control rats (unilaterally nephrectomized) and in solitary transplanted left kidneys (unilaterally nephrectomized recipients) ten days post-nephrectomy or post-transplant. Kidneys were flushed and transplanted immediately (0 hours) or flushed with and stored in the same solution for 24 hours as indicated. See text for description of the solutions.

Although the present invention has been described for applications involving the transplantation of kidneys and, more specifically, rat kidneys, the flush-storage solutions of the present invention can be utilized in the transplantation of other organs as well. In addition, as noted above, the present invention provides an improved method of flushing and storing donor organs as well as an improved method of transplanting donor organs into a recipient.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A solution for flushing and/or storing donor organs comprising:
   mannitol in an amount ranging from about 50 mM to about 100 mM,
   sodium in an amount ranging from about 130 mM to about 160 mM.

2. The solution of claim 1 further comprising potassium in an amount less than 6 mM.

3. The solution of claim 1 wherein the solution has a pH ranging from about 6.6 to about 7.0 at a temperature of about 0° C.

4. The solution of claim 1 further comprising glucose in an amount less than 20 mM.

5. The solution of claim 1 further comprising lactobionate in an amount greater than 100 mM.

6. The solution of claim 1 further comprising glycine.

7. The solution of claim 1 wherein the calculated osmolality of the solution ranges from about 340 mOs/Kg to about 390 mOs/Kg.

8. The solution of claim 1 further comprising a combined concentration of $HPO_4^{-2}$ and $H_2PO_4^{-1}$ of less than 10 mM.

9. The solution of claim 1 further comprising magnesium in an amount less than 10 mM.

10. The solution of claim 1 further comprising $So_4^{-2}$ in an amount less than 10 mM.

11. The solution of claim 1 wherein the solution is substantially free of allopurinol, glutathione, adenosine and hydroxyethylstarch.

12. A solution for flushing at least a portion of a donor's blood from a donor organ and/or storing the donor organ, the solution comprising:
   sodium in an amount ranging from about 130 mM to about 160 mM and potassium in an amount ranging from about 3 mM to about 6 mM and wherein the solution has a pH ranging from about 6.6 to about 7.0 at a temperature of about 0° C. and wherein the solution is substantially free of allopurinol, glutathione, adenosine and hydroxyethylstarch.

13. The solution of claim 12 wherein the solution further comprises mannitol in an amount ranging from about 50 mM to about 100 mM.

14. The solution of claim 12 wherein the solution further comprises glucose in an amount less than 20 mM.

15. The solution of claim 12 wherein the solution further comprises lactobionate in an amount greater than 100 mM.

16. The solution of claim 12 wherein the solution further comprises glycine.

17. The solution of claim 12 wherein the calculated osmolality of the solution ranges from about 340 mOs/Kg to about 390 mOs/Kg.

18. The solution of claim 12 wherein the solution further comprises a combined concentration of $HPO_4^{-2}$ and $H_2PO_4^{-1}$ of less than 10 mM.

19. The solution of claim 12 wherein the solution further comprises magnesium in an amount less than 11 mM.

20. A solution for flushing and/or storing donor organs comprising:

| | |
| --- | --- |
| sodium | 130–160 mM |
| potassium | 3–6 mM |
| magnesium | 0–5 mM |
| lactobionate | 100–150 mM |
| sulfate | 0–5 mM |
| phosphate | 0–10 mM |
| glucose | 0–10 mM |
| mannitol | 50–100 mM |
| glycine | 0–5 mM. |

21. The solution of claim 20 wherein the pH of the solution ranges from about 6.7 to about 6.9 at a temperature of about 0° C.

22. The solution of claim 20 wherein the calculated osmolality of the solution ranges from about 340 mOs/Kg to about 390 mOs/Kg.

23. A method of transplanting a donor organ into a recipient patient, the method comprising the following steps:
   harvesting the organ from a donor;

flushing the donor's blood out of the organ with a solution comprising mannitol in an amount ranging from about 50 mM to about 100 mM, sodium in an amount ranging from about 130 mM to about 160 mM and wherein the solution has a pH ranging from about 6.6 to about 7.0 at a temperature of about 0° C.;

storing the organ in said solution; and transplanting the organ in the recipient.

24. A method of preparing a donor organ for transplantation, the method comprising the following steps:

flushing the donor's blood out of the organ with a solution comprising mannitol in an amount ranging from about 50 mM to about 100 mM and sodium in an amount ranging from about 130 mM to about 160 mM, wherein the solution is substantially free of allopurinol, glutathione, adenosine and hydroxyethylstarch; and storing the organ in said solution.

* * * * *

UNITED STATES PATENT AND TRADEMARK OFFICE
CERTIFICATE OF CORRECTION

PATENT NO. : 5,834,178 C1
DATED : April 23, 2002
INVENTOR(S) : Paul C. Churchill et al.

It is certified that error appears in the above-identified patent and that said Letters Patent is hereby corrected as shown below:

Column 2,
Line 16, delete "sodium 130" and insert -- sodium --

Signed and Sealed this

First Day of October, 2002

*Attest:*

*Attesting Officer*

JAMES E. ROGAN
*Director of the United States Patent and Trademark Office*

(12) REEXAMINATION CERTIFICATE (4557th)
United States Patent
Churchill et al.

(10) Number: US 5,834,178 C1
(45) Certificate Issued: Apr. 23, 2002

(54) FLUSH-STORAGE SOLUTION FOR DONOR ORGANS

(75) Inventors: Paul C. Churchill, Troy; Monique C. Churchill, St. Clair Shores, both of MI (US)

(73) Assignee: Wayne State University, Detroit, MI (US)

Reexamination Request:
No. 90/005,405, Jun. 24, 1999

Reexamination Certificate for:
Patent No.: 5,834,178
Issued: Nov. 10, 1998
Appl. No.: 08/890,269
Filed: Jul. 9, 1997

(51) Int. Cl.⁷ .................................................. A01N 1/02
(52) U.S. Cl. .......................................... 435/1.2; 435/1.1
(58) Field of Search .......................... 435/1.2, 325, 1.1; 514/23

(56) References Cited

FOREIGN PATENT DOCUMENTS

| | | |
|---|---|---|
| EP | 0 356 367 A | 2/1990 |
| EP | 0 664 080 A | 7/1995 |
| GB | 2 270 614 A | 3/1994 |
| WO | WO 86/00812 | 2/1986 |
| WO | WO 92/12722 A | 8/1992 |
| WO | WO 93/02653 A | 2/1993 |
| WO | WO 94/28950 | 9/1994 |
| WO | WO 95/05076 | 2/1995 |
| WO | WO 96/19918 | 7/1996 |

*Primary Examiner*—Jennifer Graser

(57) ABSTRACT

A flush-storage solution for flushing blood out of a donor organ and cold-storing the donor organ prior to transplantation is provided. The solution of the present invention includes mannitol as an impermeable solute. The present invention also provides an improved method of flushing and cold-storing donor organs as well as an improved method of transplanting donor organs into a recipient.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 24 is confirmed.

Claims 2 and 13 are cancelled.

Claims 1, 11, 12, 20 and 23 are determined to be patentable as amended.

Claims 3–10, 14–19, 21 and 22, dependent on an amended claim, are determined to be patentable.

1. A solution for flushing and/or storing donor organs comprising:
   mannitol in an amount ranging from about 50 mM to about 100 mM,
   sodium in an amount ranging from about 130 mM to about 160 mM, *potassium in an amount less than 6 mM,*
   *the solution further being substantially free of hydroxyethylstarch.*

11. The solution of claim 1 wherein the solution is substantially free of allopurinol, glutathione, *and* adenosine [and hydroxyethylstarch].

12. A solution for flushing at least a portion of a donor's blood from a donor organ and/or storing the donor organ, the solution comprising:
    sodium in an amount ranging from about 130 mM to about 160 mM, [and]
    potassium in an amount ranging from about 3 mM to about 6 mM,
    *mannitol in an amount ranging from about 50 mM to about 100 mM,*
    and wherein the solution has a pH ranging from about 6.6 to about 7.0 at a temperature of about 0° C. and wherein the solution is substantially free of allopurinol, glutathione, adenosine and hydroxyethylstarch.

20. A solution for flushing and/or storing donor organs comprising:

| sodium | 130–160 mM |
| --- | --- |
| potassium | 3–6 mM |
| magnesium | 0–5 mM |
| lactobionate | 100–150 mM |
| sulfate | 0–5 mM |
| phosphate | 0–10 mM |
| glucose | 0–10 mM |
| mannitol | 50–100 mM |
| glycine | 0–5 mM, |

*the solution further being substantially free of hydroxyethylstarch.*

23. A method of transplanting a donor organ into a recipient patient, the method comprising the following steps:
    harvesting the organ from a donor;
    flushing the donor's blood out of the organ with a solution comprising mannitol in an amount ranging from about 50 mM to about 100 mM, sodium in an amount ranging from about 130 mM to about 160 mM and wherein the solution has a pH ranging from about 6.6 to about 7.0 at a temperature of about 0° C. *and the solution further being substantially free of hydroxyethylstarch*;
    storing the organ in said solution; and
    transplanting the organ in the recipient.

* * * * *